United States Patent
Ryles et al.

(10) Patent No.: US 6,280,708 B1
(45) Date of Patent: Aug. 28, 2001

(54) STABLE PEROXIDE DENTAL COMPOSITIONS

(75) Inventors: Christine Watson Ryles, Milford; David Robert Williams, Monroe, both of CT (US)

(73) Assignee: Unilever Home & Personal Care USA, division of Conopco, Greenwich, CT (US)

( * ) Notice: Subject to any disclaimer, the term of this patent is extended or adjusted under 35 U.S.C. 154(b) by 0 days.

(21) Appl. No.: 09/546,012

(22) Filed: Apr. 10, 2000

Related U.S. Application Data

(60) Provisional application No. 60/155,700, filed on Sep. 23, 1999.

(51) Int. Cl.$^7$ ................ A61K 7/16; A61K 7/20
(52) U.S. Cl. .................................................. 424/53
(58) Field of Search .......................... 424/49–58

(56) References Cited

FOREIGN PATENT DOCUMENTS

00/42981   7/2000   (WO) .

*Primary Examiner*—Shep K. Rose
(74) *Attorney, Agent, or Firm*—Milton L. Honig

(57) ABSTRACT

An oral composition is provided containing stabilized peroxide ingredients. Stabilization is achieved by combination of a triphenyl methane dye and potassium nitrate. Particularly useful as the dye are FD&C Blue 1 and FD&C Green 3.

5 Claims, No Drawings

STABLE PEROXIDE DENTAL COMPOSITIONS

This Appln claims the benefit of Provisional No. 60/155,700 filed Sep. 23, 1999.

BACKGROUND OF THE INVENTION

1. Field of the Invention

The invention relates to peroxide containing dentifrices stabilized against decomposition.

2. The Related Art

Peroxides are widely viewed by the dental profession as an effective treatment against gum disease. Periodontal disorders are believed to arise from infectious anaerobic microorganisms which are active in the absence of oxygen. These microorganisms can be controlled or entirely eliminated by contact with peroxides which release oxygen. According to this rationale, oxygen creates an aerobic atmosphere destructive to the microorganisms.

Facile reactivity of the peroxide benefits performance but conversely results in storage stability problems. Dentifrices containing peroxides tend to decompose within a relatively short period of time. Not only is activity lost but there can be a marked breakdown in the dentifrice's physical properties. Dentifrice viscosity is particularly adversely affected by the chemical breakdown of thickening agents. A variety of techniques have been developed to counter the problem.

U.S. Pat. No. 4,226,851 (Sompayrac) discloses oral compositions comprising hydrogen peroxide and zinc chloride wherein vitamin E is added as a stabilizing agent. U.S. Pat. No. 4,788,052 and U.S. Pat. No. 4,839,157 both to Ng et al. report aqueous hydrogen peroxide gel dentifrices stabilized with a combination of hydrophilic and hydrophobic fumed silica.

U.S. Pat. No. 5,059,417 (Williams et al.) reports on clear gel dentifrices having a criticality in their ratio of glycerol to polyoxyethylene-polyoxypropylene copolymer. Phosphoric acid is indicated to be beneficial as an acidifying agent.

Tin compounds are described in U.S. Pat. No. 5,217,710 (Williams et al.) as stabilizing fluoride induced gel decomposition.

U.S. Pat. No. 5,326,494 and U.S. Pat. No. 5,180,517, both to Woods, describe arylazo compounds, such as tartrazine, for stabilizing sodium perborate containing cleaning liquids.

U.S. Pat. No. 5,846,570 (Barrow et al.) discloses the use of dyes such as FD&C Blue 1 and FD&C Green 3 for stabilization of hydrogen peroxide containing dentifrice gels.

Yet even with the many advances in the field, there remains a need to discover improved systems. Consequently, systems have been sought for use in oral compositions that impart to the consumer satisfactory taste, contribute no disruptive influence upon rheology, and maintain active peroxide levels even under stressing temperature conditions.

Accordingly, it is an object of the present invention to provide a peroxide containing oral composition that maintains peroxide stability even at elevated temperatures over extended periods of time.

Another object of the present invention is to provide a peroxide containing oral composition that maintains viscosity even after extended storage.

These and other objects of the present invention will become more readily apparent upon consideration of the summary, detailed descriptions and examples which follow.

SUMMARY OF THE INVENTION

An oral composition is provided which includes:
(i) from about 0.001 to about 20% by weight of a peroxide;
(ii) from about 0.5 to about 20% by weight of potassium nitrate;
(iii) from about 0.00001 to about 1% by weight of a triphenyl methane dye; and
(iv) a pharmaceutically acceptable carrier.

DETAILED DESCRIPTION OF THE INVENTION

Now it has been found that peroxides in oral compositions can be stabilized with a combination of potassium nitrate and triphenyl methane dyes, particularly with FD&C Blue 1 or FD&C Green 3.

Potassium nitrate is a well-known dental ingredient. Commonly it is utilized as a tooth desensitizing agent. U.S. Pat. No. 3,863,006 and U.S. Pat. No. 4,400,373 to Hodosh are the seminal patents disclosing the use of this material. It was claimed for desensitizing hypersensitive dentin and cementum as well as for reducing gingival bleeding.

While investigating the use of potassium nitrate for its traditional use, it was discovered that the substance in combination with triphenyl methane dyes could stabilize peroxides against decomposition. Thus, compositions of this invention will include potassium nitrate at levels ranging from about 0.5 to about 20%, preferably from about 1 to about 10%, optimally from about 3 to about 7% by weight.

Triphenyl methane dyes employed in the present invention have the structure:

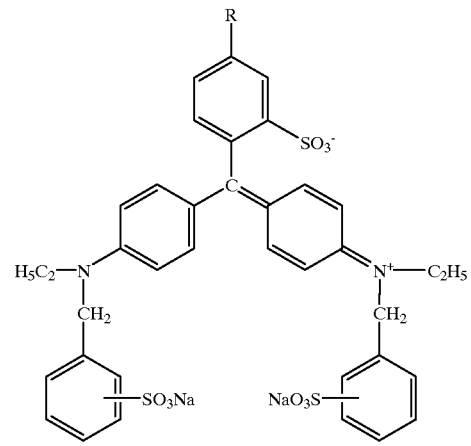

wherein R is a hydrogen, hydroxyl, carboxyl or acyloxy radical. Most preferred is when R is either hydrogen representing FD&C Blue 1 or hydroxy representing FD&C Green 3. Amounts of the dye will range from about 0.00001 to about 1%, preferably from about 0.0001 to about 0.1%, optimally from about 0.001 to about 0.01% by weight.

Another essential component of the present invention is that of a peroxide. Ordinarily the peroxide will be hydrogen peroxide but it may also be selected from the group consisting of urea peroxide, calcium peroxide, sodium peroxide, sodium percarbonate, sodium perborate and $C_2$–$C_{30}$ organic peroxyacids (e.g. peracetic acid) and combinations thereof. Amounts of the peroxide may range from about 0.001 to about 20%, preferably from about 0.01 to about 15%, more preferably from about 0.1 to about 10%, optimally from about 0.5 to about 8% by weight.

Chelating acids may also be present to stabilize against peroxide decomposition. Typical chelating acids include citric acid, lactic acid, malic acid, fumaric acid, tartaric acid, phosphoric acid and mixtures thereof. Most preferred is phosphoric acid. Amounts of the chelating acid may range from about 0.001 to about 5%, preferably from about 0.01 to about 2%, optimally from about 0.1 to about 1% by weight. The compositions of the present invention may either be in paste, gel or liquid form. Most preferably it is in gel form.

A further essential component of the present invention is that of a pharmaceutically acceptable carrier. The carrier may include such functional ingredients as water, humectants, abrasives, thickeners and surfactants. Total levels of these materials may range anywhere from 0.1 to 99.9%, preferably from 20 to 99% by weight.

Oral compositions of the present invention may further include bicarbonate salts in the same or in a separate composition from that of the peroxide. Most preferably, the peroxide will be in a separate composition from that of the bicarbonate. In those situations, each composition is held within a separate compartment available for simultaneous delivery and substantially equal volumes for use in the mouth.

The bicarbonate compositions may also contain a fluoride anticaries compound. Especially preferred is sodium fluoride. Bicarbonate salts will usually be present in alkali metal form, examples of which are sodium and potassium. Typically, the concentration of bicarbonate salt will range from about 0.5 to about 80%, preferably from about 1 to about 50%, optimally between about 2 and about 20% by weight of the total combined dental product. The pH of the bicarbonate composition may range from about 7.0 to about 9.5, most preferably about 8.0 to about 9.0. Typically the bicarbonate composition will include a natural or synthetic thickening agent in an amount about 0.1 to about 10%, preferably about 0.5 to about 5% by weight. Thickeners can be selected from hydroxypropyl methyl cellulose, hydroxyethyl cellulose, sodium carboxymethyl cellulose, xanthan gum, tragacanth gum, karaya gum, arabic gum, Irish moss, starch, alginates and carrageenans.

Water may be present in the compositions in amounts ranging from about 5 to about 99% by weight. When the peroxide composition is a gel, the amount of water may range from about 20 to about 55%, optimally between 35 and 45% by weight.

Humectants are usually polyols which, for example, may include glycerol, sorbitol, propylene glycol, lactitol, xylitol, polypropylene glycol, polyethylene glycol, hydrogenated corn syrup and mixtures thereof. Generally the amount of humectant will range from about 5 to about 90%, preferably from about 20 to about 70% by weight.

When the peroxide compositions are in the form of a gel, it may be desirable to utilize a thickening agent that is a combination of water and a crosslinked acrylic polymer and/or a polyoxyethylene/polyoxypropylene copolymer. Most preferred is the polyoxyethylene/polyoxypropylene copolymer, especially one having a hydrophobic portion, represented by ($C_3H_6O$), with a molecular weight range from about 2,750 to 4,000 and a hydrophilic portion, represented by ($C_2H_4O$), constituting about 70–80% of the weight of the copolymer.

Commercially, the above mentioned copolymers are available from the BASF Corporation under the trademark, Pluronic F88, F99, F108 and F127. Most preferred is Pluronic F127 (more commonly described by its CTFA name, Poloxamer 407) which has a molecular weight ranging from about 10,000 to about 15,000, and containing about 70% of the hydrophilic polyoxyethylene moiety. Amounts of the copolymer can range anywhere from about 18 to about 25% by weight, preferably between about 19 and about 24%. Poloxamers are particularly suitable for this invention because of their wide pH tolerance, high compatibility with hydrogen peroxide and unique gel properties.

The carrier may include an abrasive. Illustrative abrasives are, silicas, aluminas, calcium carbonate and salts of metaphosphate. Especially preferred are alumina and silica. Amounts of the abrasive may range from about 5 to about 80% by weight.

Surfactants may also be a constituent of the pharmaceutically acceptable carrier. The surfactant may be of the anionic, nonionic, cationic or amphoteric type. Most preferred are sodium lauryl sulphate, sodium dodecylbenzene sulphonate and sodium laurylsarcosinate. Surfactants are usually present in amounts from about 0.5 to about 10%, preferably from about 1 to about 5% by weight.

Tartar control agents may be incorporated into compositions of this invention, especially effective will be zinc salts (e.g. zinc citrate trihydrate) and agents containing phosphorous. Inorganic phosphorous tartar control agents may include any of the pyrophosphates such as disodium pyrophosphate, dipotassium pyrophosphate, tetrapotassium pyrophosphate, tetrasodium pyrophosphate and mixtures thereof. Organic phosphorous compounds that may serve as tartar control agents include polyphosphonates such as disodium ethane-1-hydroxy-1,1-diphosphonate (EHDP), methanediphosphonic acid, and 2-phosphonobutane-1,2,4-tricarboxylic acid.

For anti-caries protection, a source of fluoride ion may be present. Fluoride sources include sodium fluoride, potassium fluoride, calcium fluoride, stannous fluoride, stannous monofluorophosphate and sodium monofluorophosphate. These sources should release anywhere from 25 to 3500 ppm of fluoride ion. The anti-caries agent may be present in an amount from about 0.05 to about 3%, preferably about 0.2 to about 1% by weight of the composition.

Sweetening agents such as saccharin, sodium cyclamate, aspartame, sucrose and the like may be included at levels from about 0.1 to about 5% by weight.

Other additives may also be incorporated into the oral compositions including preservatives, silicones and other synthetic or natural polymers such as Gantrez S-97.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight of the total composition unless otherwise stated.

EXAMPLE 1

Typical of the present invention is a peroxide gel composition whose formulation is detailed under Table I. The formulation of Table I may be utilized either separately or in combination with a bicarbonate composition detailed under Table II, each of the compositions being held in a separate compartment of a dual compartment dispenser.

TABLE I

Peroxide Gel Component

| INGREDIENT | WEIGHT % |
|---|---|
| Glycerin | 45.00 |
| FD&C Blue #1 | 0.01 |
| Methyl Salicylate | 0.50 |
| Phosphoric Acid | 0.15 |
| Hydrogen Peroxide (35% Active) | 4.285 |
| Potassium Nitrate | 5.00 |
| Pluronic F-127 (Polyoxyethylene/Polyoxypropylene) | 22.0 |
| Deionized Water | Balance |

TABLE II

Bicarbonate Paste Component

| INGREDIENT | WEIGHT % |
|---|---|
| Polyol II (Sorbitol) | 46.30 |
| Potassium Nitrate | 5.00 |
| Sodium Lauryl Sulphate | 2.98 |
| Ethanol | 2.85 |
| Sodium Saccharin | 0.54 |
| Sodium Fluoride | 0.44 |
| Menthol, USP-Natural | 0.50 |
| Flavor | 1.30 |
| Titanium Dioxide | 0.30 |
| Cellulose Gum (CNC) | 0.80 |
| Sylox 15X | 9.00 |
| Syloid 63XX | 10.00 |
| Sodium Bicarbonate | 5.00 |
| Deionized Water | balance |

EXAMPLE 2

A series of stability experiments were conducted to evaluate the effect of potassium nitrate in combination with FD&C Blue 1 in a peroxide gel composition.

The test employed was the Peroxide Stability/Stress Test (PSST). Samples were exposed to accelerated aging at a temperature of 95° C. over a 12 hour period. These aging conditions were found to have good correlation with 3 month storage stability testing at 105° F. Peroxide content of the gel was assayed by oxidizing potassium iodide to iodine and titrating with sodium thiosulphate on an auto-titrator fitted with redox electrode.

Gel compositions having the same composition (Sample A) as that identified under Table I of Example 1 were herein evaluated. As control experiments, Sample B omitted the blue dye while Sample C omitted the potassium nitrate. Table III outlines the results of these tests.

TABLE III

Peroxide Stability Results

| SAMPLE | ACTIVE COMPONENTS | % PEROXIDE RECOVERY |
|---|---|---|
| A | Peroxide/Dye/Potassium Nitrate | 93.61 |
| B | Peroxide/Potassium Nitrate | 85.88 |
| C | Peroxide/Dye | 88.58 |

Evident from Table III is that an improved stability can be achieved by the presence of a combination of dye and potassium nitrate. Each of those materials alone is less effective.

The foregoing description and examples illustrate selected embodiments of the present invention. In light thereof variations and modifications will be suggested to one skilled in the art, all of which are within the spirit and purview of this invention.

What is claimed is:

1. An oral composition comprising:
   (i) from about 0.001 to about 20% by weight of a peroxide;
   (ii) from about 0.5 to about 20% by weight of potassium nitrate;
   (iii) from about 0.00001 to about 1% by weight of a triphenyl methane dye; and
   (iv) a pharmaceutically acceptable carrier, all three elements (i) through (iii) being mixed and stabilized together in the carrier, said potassium nitrate and triphenylmethane dye combining to stabilize said peroxide against decomposition.

2. The composition according to claim 1 wherein the peroxide is selected from the group consisting of hydrogen peroxide, urea peroxide, calcium peroxide, sodium peroxide, sodium percarbonate, sodium perborate, $C_2$–$C_{30}$ organic peroxyacids and combinations thereof.

3. The composition according to claim 1 wherein the triphenyl methane dye is selected from the group consisting of FD&C Blue 1 and FD&C Green 3.

4. The composition according to claim 1 wherein the peroxide is hydrogen peroxide.

5. The composition according to claim 1 wherein the peroxide is in a gel form.

* * * * *